US 7,205,259 B2
Apr. 17, 2007

(12) United States Patent
Soerens (54) ABSORBENT BINDER DESICCANT COMPOSITION AND ARTICLES INCORPORATING IT

(75) Inventor: Dave Allen Soerens, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 164 days.

This patent is subject to a terminal disclaimer.

(21) Appl. No.: 10/622,752

(22) Filed: Jul. 18, 2003

(65) Prior Publication Data

US 2004/0106721 A1    Jun. 3, 2004

Related U.S. Application Data (63) Continuation-in-part of application No. 10/427,809, filed on May 1, 2003, now Pat. No. 6,887,961, which is a continuation-in-part of application No. 10/324,478, filed on Dec. 20, 2002, now Pat. No. 6,849,685, which is a continuation-in-part of application No. 10/206,883, filed on Jul. 26, 2002, now Pat. No. 6,737,491.

(51) Int. Cl.
*B01J 20/00*     (2006.01)

(52) U.S. Cl. .................................... 502/407

(58) Field of Classification Search ............... 502/400, 502/401, 402, 407
See application file for complete search history.

(56) References Cited

U.S. PATENT DOCUMENTS

| | | | |
|---|---|---|---|
| 3,617,362 A | 11/1971 | Bemmels et al. |
| 3,951,893 A | 4/1976 | Gander |
| 3,959,242 A | 5/1976 | Watts et al. |
| 3,963,605 A | 6/1976 | Seabourn |
| 3,963,805 A | 6/1976 | Chu |
| 4,251,643 A | 2/1981 | Harada et al. |
| 4,291,136 A | 9/1981 | Keogh |
| 4,328,323 A | 5/1982 | Keogh |
| 4,343,917 A | 8/1982 | Keogh |
| 4,353,997 A | 10/1982 | Keogh |
| 4,369,289 A | 1/1983 | Keogh |
| 4,408,011 A | 10/1983 | Barnabeo |
| 4,434,272 A | 2/1984 | Keogh |
| 4,440,907 A | 4/1984 | Keogh |
| 4,446,279 A | 5/1984 | Keogh |
| 4,459,396 A | 7/1984 | Yamasaki et al. |
| 4,489,029 A | 12/1984 | Keogh et al. |
| 4,493,924 A | 1/1985 | Rifi |
| 4,502,968 A | 3/1985 | Noda et al. |
| 4,526,930 A | 7/1985 | Keogh |
| 4,551,504 A | 11/1985 | Barnabeo |
| 4,575,535 A | 3/1986 | Keogh |
| 4,579,913 A | 4/1986 | Keogh |
| 4,589,876 A | 5/1986 | Van Tilburg |
| 4,593,071 A | 6/1986 | Keogh |
| 4,676,820 A | 6/1987 | Le Sergent et al. |
| 4,753,993 A | 6/1988 | Keogh |
| 4,767,820 A | 8/1988 | Keogh |
| 4,806,594 A | 2/1989 | Gross et al. |
| 4,921,136 A | 5/1990 | Roggenburg, Jr. |
| 4,940,646 A | 7/1990 | Pawlowski |
| 5,047,476 A | 9/1991 | Keogh |
| 5,089,564 A | 2/1992 | Bullen |
| 5,112,919 A | 5/1992 | Furrer et al. |
| 5,145,906 A | 9/1992 | Chambers et al. |
| 5,196,470 A | 3/1993 | Anderson et al. |
| 5,204,404 A | 4/1993 | Werner, Jr. et al. |
| 5,354,829 A | 10/1994 | Swisher et al. |
| 5,364,382 A | 11/1994 | Latimer et al. |
| 5,389,728 A | 2/1995 | Prejean |
| 5,532,350 A | 7/1996 | Cottrell et al. |
| 5,656,132 A | 8/1997 | Farrington, Jr. et al. |
| 5,853,867 A | 12/1998 | Harada et al. |
| 5,859,074 A | 1/1999 | Rezai et al. |
| 5,911,937 A | 6/1999 | Hekal |
| 5,932,668 A | 8/1999 | Friebe et al. |
| 5,945,476 A | 8/1999 | Roesler et al. |
| 5,961,763 A | 10/1999 | Makoui et al. |

(Continued)

FOREIGN PATENT DOCUMENTS

CA           756190           4/1967

(Continued)

OTHER PUBLICATIONS

American Society for Testing Materials (ASTM) Designation: D1003-00, "Standard Test Method for Haze and Luminous Transmittance of Transparent Plastics," pp. 1-6, Published Jul. 2000.
Neumann, A.W., and R.J. Good, "Techniques of Measuring Contact Angles," Chapter 2, Surface and Colloid Science—Experimental Methods, vol. 11, edited by R.J. Good and R.R. Stromberg, Plenum Press, 1979, pp. 31-91, no month.

*Primary Examiner*—Edward M. Johnson
(74) *Attorney, Agent, or Firm*—Pauley Petersen & Erickson (57) ABSTRACT

An absorbent binder desiccant composition is provided which is capable of spontaneous crosslinking after application to a substrate, at a temperature of about 120° C. or less. The absorbent binder desiccant composition includes a monoethylenically unsaturated polymer, such as carboxylic acid, sulphonic acid, or phosphoric acid, or salts thereof, or a quaternary ammonium salt, and an acrylate or methacrylate ester that contains an alkoxysilane functionality, or a monomer capable of co-polymerization with a compound containing a trialkoxy silane functional group and subsequent reaction with water to form a silanol group, and a desiccant component. The absorbent binder desiccant composition is particularly suitable for use in manufacturing a wide variety of humidity control articles.

35 Claims, 2 Drawing Sheets

U.S. PATENT DOCUMENTS

| | | | |
|---|---|---|---|
| 6,013,855 | A | 1/2000 | McPherson et al. |
| 6,020,071 | A | 2/2000 | Watson |
| 6,020,171 | A | 2/2000 | Saito et al. |
| 6,054,523 | A | 4/2000 | Braun et al. |
| 6,110,533 | A | 8/2000 | Coté et al. |
| 6,183,872 | B1 | 2/2001 | Tanaka et al. |
| 6,200,684 | B1 | 3/2001 | Yamaguchi et al. |
| 6,214,274 | B1 | 4/2001 | Melius et al. |
| 6,300,275 | B1 | 10/2001 | Weir |
| 6,315,765 | B1 | 11/2001 | Datta et al. |
| 6,380,298 | B2 | 4/2002 | Flautt et al. |
| 6,387,084 | B1 | 5/2002 | VanGompel et al. |
| 6,403,857 | B1 | 6/2002 | Gross et al. |
| 6,417,425 | B1 | 7/2002 | Whitmore et al. |
| 6,458,877 | B1 | 10/2002 | Ahmed et al. |
| 6,464,675 | B2 | 10/2002 | De Carvalho |
| 6,497,690 | B2 | 12/2002 | Haarer |
| 6,534,572 | B1 | 3/2003 | Ahmed et al. |
| 6,596,402 | B2 | 7/2003 | Soerens et al. |
| 6,689,934 | B2 | 2/2004 | Dodge et al. |
| 6,737,491 | B2 | 5/2004 | Soerens et al. |
| 6,808,801 | B2 | 10/2004 | George et al. |
| 6,822,135 | B2 | 11/2004 | Soerens et al. |
| 6,849,685 | B2 | 2/2005 | Soerens et al. |
| 6,887,961 | B2 | 5/2005 | Soerens et al. |
| 6,964,803 | B2 | 11/2005 | Krautkramer et al. |
| 2002/0049417 | A1 | 4/2002 | Onishi et al. |
| 2002/0090453 | A1 | 7/2002 | Muthiah et al. |
| 2003/0008989 | A1 | 1/2003 | Gore et al. |
| 2003/0100875 | A1 | 5/2003 | Suekane et al. |
| 2003/0149413 | A1 | 8/2003 | Mehawej |
| 2004/0019339 | A1 | 1/2004 | Ranganathan et al. |
| 2004/0043688 | A1 | 3/2004 | Soerens et al. |
| 2004/0106721 | A1 | 6/2004 | Soerens |
| 2004/0116014 | A1 | 6/2004 | Soerens et al. |
| 2004/0116885 | A1 | 6/2004 | Soerens et al. |
| 2004/0122390 | A1 | 6/2004 | Soerens et al. |

FOREIGN PATENT DOCUMENTS

| | | |
|---|---|---|
| EP | 0 132 910 A2 | 2/1985 |
| EP | 0 475 664 A1 | 3/1992 |
| EP | 0 705 861 A1 | 4/1996 |
| EP | 0 844 265 A1 | 5/1998 |
| EP | 0 992 252 | 4/2000 |
| EP | 1 013 291 A1 | 6/2000 |
| EP | 1 059 320 A2 | 12/2000 |
| EP | 1 138 293 A1 | 10/2001 |
| EP | 1 199 059 | 4/2002 |
| EP | 1 529 508 A2 | 5/2005 |
| WO | 99/57201 | 11/1999 |
| WO | WO 02/053664 A2 | 7/2002 |

ABSORBENT BINDER DESICCANT COMPOSITION AND ARTICLES INCORPORATING IT

This application is a continuation-in-part of U.S. patent application Ser. No. 10/427,809, filed 1 May 2003 now U.S. Pat. No 6,887,961, which in turn is a continuation-in-part of U.S. patent application Ser. No. 10/324,478, filed 20 Dec. 2002 now U.S. Pat. No. 6,849,685, which in turn is a continuation-in-part of U.S. patent application Ser. No. 10/206,883, filed 26 Jul. 2002 now U.S. Pat. No. 6,737,491. The disclosures of the three prior applications are incorporated herein by reference.

BACKGROUND OF THE INVENTION

This invention is directed to an absorbent binder desiccant composition and structure, a method of making the absorbent binder desiccant composition and structure, and articles which utilize the composition and structure.

Adhesives, or binders, are a necessary element of many products. While adhesives beneficially hold products together, adhesives may also have a tendency to interfere with the absorbency of fluids in absorbent products. Adhesives are typically hydrophobic and therefore are not conducive to absorbency or liquid transfer functions.

Hydrophilic adhesives are known, such as adhesives formulated from water-soluble polymers such as poly(vinyl alcohol), poly(vinyl methyl ether), poly(vinyl pyrrolidone), poly(ethylene oxide), or cellulose derivatives such as hydroxypropyl cellulose. Dextrans, starches and vegetable gums have been used to provide hydrophilic adhesives. These materials provide adhesion under dry conditions. However, upon exposure to aqueous fluids, these materials lose bonding capability because they are substantially soluble in aqueous fluids.

Recent development efforts have provided coating materials for a variety of uses. For example, U.S. Pat. No. 6,054,523, to Braun et al., describes materials that are formed from organopolysiloxanes containing groups that are capable of condensation, a condensation catalyst, an organopolysiloxane resin, a compound containing a basic nitrogen, and polyvinyl alcohol. The materials are reported to be suitable for use as hydrophobic coatings and for paints and sealing compositions.

Anderson et al., in U.S. Pat. No. 5,196,470, reported an alcohol-based, water-soluble binder composition. Because this composition is water-soluble and not cross-linked, it has no absorbency.

Others have reported the production of graft copolymers having silane functional groups that permitted the initiation of cross-linking by exposure to moisture. Prejean (U.S. Pat. No. 5,389,728) describes a melt-processible, moisture-curable graft copolymer that was the reaction product of ethylene, a 1–8 carbon alkyl acrylate or methacrylate, a glycidyl containing monomer such as glycidyl acrylate or methacrylate, onto which has been grafted N-tert-butylaminopropyl trimethoxysilane. The resulting copolymers were reported to be useful as adhesives and for wire and cable coatings.

Furrer et al., in U.S. Pat. No. 5,112,919, reported a moisture-crosslinkable polymer that was produced by blending a thermoplastic base polymer, such as polyethylene, or a copolymer of ethylene, with 1-butene, 1-hexene, 1-octene, or the like; a solid carrier polymer, such as ethylene vinylacetate copolymer (EVA), containing a silane, such as vinyltrimethoxysilane; and a free-radical generator, such as an organic peroxide; and heating the mixture. The copolymers could then be cross-linked by reaction in the presence of water and a catalyst, such as dibutyltin dilaurate, or stannous octoate.

U.S. Pat. No. 4,593,071 to Keough reported moisture cross-linkable ethylene copolymers having pendant silane acryloxy groups. The resultant cross-linked polymers were reported to be especially resistant to moisture and to be useful for extruded coatings around wires and cables. The same group has reported similar moisture curable polymers involving silanes in U.S. Pat. Nos. 5,047,476, 4,767,820, 4,753,993, 4,579,913, 4,575,535, 4,551,504, 4,526,930, 4,493,924, 4,489,029, 4,446,279, 4,440,907, 4,434,272, 4,408,011, 4,369,289, 4,353,997, 4,343,917, 4,328,323, and 4,291,136.

U.S. Pat. No. 5,204,404 to Werner reported crosslinkable hydrophobic acrylate ester copolymers including 0.1 to 10% acrylic acid. The resultant cross-linked polymers were reported to be useful for painting and refinishing the exterior of automobiles.

Non-absorbent polymers have been mixed with desiccants for use in humidity control packaging and the like. U.S. Pat. No. 5,911,937, issued to Hekal, discloses a blend of a matrix polymer, desiccating agent and channeling agent. The matrix polymer can be polyethylene or polypropylene. The desiccating agent can be an anhydrous salt (or other material which absorbs water) or a compound which chemically reacts with water. The channeling agent transports water from the exterior of the matrix polymer to the desiccating agent within the matrix polymer. Suitable channeling agents include ethylene vinyl alcohol and polyvinyl alcohol. U.S. Pat. No. 6,174,952, issued to Hekal, discloses a structure including a matrix polymer, desiccating agent, and interconnecting channels, wherein the desiccating agent is distributed within the channels.

There is a need or desire for a polymeric desiccant composition having binder properties, which is relatively easy and inexpensive to apply and use.

SUMMARY OF THE INVENTION

The present invention is directed to an absorbent binder desiccant composition and a resulting absorbent binder desiccant structure. The absorbent binder desiccant composition includes an absorbent binder (polymer matrix) component and a desiccant component. The absorbent binder component is a self-crosslinking hydrophilic polymer which can be applied to a substrate in a liquid or other flowable form. The self-crosslinking polymer is mixed with the desiccant component. After applying the mixture to a substrate, the polymer can be crosslinked to form an absorbent binder component which is bound to the substrate. Alternatively, the absorbent binder component may be applied to the substrate and dried, without crosslinking.

The resulting absorbent binder desiccant structure has particles, fibers or other domains of the desiccant component dispersed within the absorbent binder component. The absorbent binder component absorbs liquid (e.g., water) or vapor from the surroundings and carries it to the desiccant component via diffusion, thus eliminating the need for a channeling agent or channels. The binding feature of the absorbent binder component eliminates the need for a separate adhesive, allowing easy application and binding of the absorbent binder desiccant composition to a wide variety of substrates.

The absorbent binder component provides a water-soluble ionic polymer capable of sufficient spontaneous crosslinking within about 10 minutes, at a temperature of about 120° C. or less, to reach an absorbent capacity of at least one gram of fluid per gram of absorbent binder component. Thereafter, the ionic polymer continues to crosslink until full absorbent capacity is reached. The ionic polymer may bear a positive or negative charge, or both.

The absorbent binder component includes at least 15 mass percent monoethylenically unsaturated monomer or polymer containing the monomer, such as carboxylic acid, sulphonic acid, phosphoric acid, or salts thereof, or a quaternary ammonium salt; and a second monomer. The second monomer can be a) a monomer capable of copolymerization which by subsequent reaction can incorporate a silane functional group capable of reaction with water to form a silanol group, and/or b) a monomer that includes a group readily transformed into a silanol functionality by subsequent reaction with water. Upon exposure to water, the silanol functional group condenses to form a crosslinked polymer. Thus, the absorbent binder component provides enhanced adhesion in a wet condition, as well as absorbency.

In one embodiment, the absorbent binder component is a flexible absorbent binder component (useful in a wide variety of applications requiring flexibility and conformability) including about 15 to about 99.8% by mass of monoethylenically unsaturated polymer units. Suitable monoethylenically unsaturated polymers include without limitation carboxylic acid, sulphonic acid, phosphonic acid, salts of the foregoing, and quaternary ammonium salts. The flexible absorbent binder component also includes about 0.1 to about 20% by mass of acrylate or methacrylate ester units that include an alkoxysilane functionality. Upon exposure to water, the alkoxysilane functionality forms a silanol group which condenses to form a crosslinked polymer.

The flexible absorbent binder component also includes about 0.1 to about 75% by mass of polyolefin glycol and/or polyolefin oxide units. The polyolefin glycol and/or oxide may include an alpha-olefin having about 2 to about 4 carbon atoms, and may include about 30 to about 15,000 olefin glycol and/or oxide units per molecule. The polyolefin glycol and/or oxide may be graft polymerized with the acrylate or methacrylate ester to form a graft copolymer. The polyolefin glycol and/or oxide may be a homopolymer or copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provides the absorbent binder desiccant structure with enhanced flexibility. Thus, the flexible absorbent binder component has enhanced adhesion in a wet condition, absorbency, and flexibility.

The absorbent binder component suitably has a glass transition temperature below about 30 degrees Celsius, or below about 10 degrees Celsius, or below about 5 degrees Celsius, and a bending modulus lower than the bending modulus of a substrate to which the absorbent binder desiccant composition is applied. Substrates include nonwoven webs, woven webs, knitted fabrics, cellulose tissue, plastic film, stranded composites, elastomer net composites, metal substrates, glass, glass fiber, and other suitable substrates. Examples of suitable plastic film substrates include those made of polypropylene, low density polyethylene, high density polyethylene, linear low density polyethylene, and ultra low density polyethylene.

The absorbent binder component can be made by polymerizing monoethylenically unsaturated monomers, one of which contains an alkoxysilane functionality. The polymerization may be induced by a variety of initiation techniques including thermal initiation, radiation initiation, or redox chemical reactions. Various types of effective radiation initiation include ultraviolet, microwave, and electron-beam radiation. The initiator generates free radicals to cause polymerization of the monomers. The resultant copolymer includes latent moisture-induced crosslinking capability by incorporation of the alkoxysilane functionality. This copolymer may be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air.

For instance, the absorbent binder component can be made by combining a first aqueous monomer solution including a reducing polymerization initiator with a second aqueous monomer solution including an oxidizing polymerization initiator wherein the initiators react to form a binder component. The polymerization of the monomer solutions to form an absorbent binder component may be carried out in about 100 minutes or less. The first aqueous monomer solution includes a monoethylenically unsaturated monomer such as a carboxylic acid salt, a sulphonic acid salt, a phosphoric acid salt or a combination thereof and an ethylenically unsaturated monomer including an acrylate or a methacrylate that contains an alkoxysilane functionality. The second aqueous monomer solution includes a monoethylenically unsaturated monomer such as a carboxylic acid salt, a sulphonic acid salt, a phosphoric acid salt or a combination thereof. Crosslinking of the resulting binder component may be induced by concentrating the combined monomer solutions through the removal of water to promote condensation of silanols generated by the hydrolysis of the alkoxysilanes.

In another embodiment, the absorbent binder component may be made by combining a first aqueous solution including a reducing polymerization initiator, a monoethylenically unsaturated monomer such as a carboxylic acid, a sulphonic acid, a phosphoric acid or a combination thereof and an ethylenically unsaturated monomer including an acrylate or a methacrylate that contains an alkoxysilane functionality with a second aqueous solution including an oxidizing polymerization initiator and a monoethylenically unsaturated monomer such as a carboxylic acid, a sulphonic acid, a phosphoric acid or a combination thereof. An amount of a basic material effective to at least partially neutralize the monoethylenically unsaturated monomer may be added to the first monomer solution and/or the second monomer solution.

The flexible absorbent binder component described above can be prepared using a template polymerization process by which the monoethyleniclly unsaturated polymer and acrylate or methacrylate ester are polymerized in the presence of a pre-formed template polymer, which is the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include without limitation ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The flexible absorbent binder component may contain the polyolefin glycol and/or oxide as a separate component, or as part of the copolymer, or a combination of both.

The flexible absorbent binder component has latent moisture-induced crosslinking capability due to the alkoxysilane functionality. The absorbent binder desiccant composition may thus be applied, in a flowable state, to a substrate or other end use application. Moisture-induced crosslinking may be accomplished through hydrolysis of the alkoxysilane and subsequent condensation upon removal of the solvent from the substrate, either by evaporation of the solvent from the substrate or using any other effective technique. Alternatively, the hydrolysis of the alkoxysilane and subsequent condensation may occur after solvent removal by exposure of the coating to moisture in ambient air.

The desiccant component of the absorbent binder desiccant composition may be any suitable desiccant. Suitable desiccants include compounds which absorb water and compounds which reversibly bond with water. To qualify as a desiccant, the compound must have sufficient affinity for water to render it capable of absorbing moisture from the surrounding atmosphere. Suitable desiccants include anhydrous salts which absorb water or moisture and form a stable hydrated salt. Other suitable desiccants include capillary desiccants which rely on fine capillaries between adjacent desiccant particles to absorb moisture.

The absorbent binder component may also have desiccant properties. For purposes of this document, the term "desiccant component" refers to a separate component which is added to the absorbent binder component, and does not refer to the absorbent binder component itself.

The desiccant component is typically mixed with the absorbent binder component before the latter is applied to a substrate or crosslinked. The resulting absorbent binder desiccant composition may be applied to any substrate useful in desiccant packaging, including plastic or paper films, fibrous nonwoven fabrics, glass, metal or the like. After application to a substrate, the absorbent binder component can be crosslinked, resulting in the absorbent binder desiccant structure of the invention, securely bound to the substrate. Alternatively, the absorbent binder component need not be crosslinked, and the absorbent binder desiccant composition may remain bound to the substrate.

With the foregoing in mind, it is a feature and advantage of the invention to provide an absorbent binder desiccant composition for easy application to a substrate, a crosslinked absorbent binder desiccant structure combined with and bound to a substrate, and an article embodying the latter.

DEFINITIONS

Within the context of this specification, each term or phrase below will include the following meaning or meanings.

"Absorbent binder desiccant composition" refers to a composition including an absorbent binder component and a desiccant component prior to crosslinking of the absorbent binder component.

"Absorbent binder desiccant structure" refers to a composition including an absorbent binder component and a desiccant component after crosslinking of the absorbent binder component.

"Binder" includes materials which are capable of attaching themselves to a substrate or are capable of attaching other substances to a substrate.

"Desiccant component" is a substance (desiccant) capable of absorbing moisture from a surrounding atmosphere. Desiccants differ from conventional absorbent and superabsorbent materials in that desiccants absorb water or water vapor in capillary channels or via chemical bonding to water, such that the absorption results in no appreciable increase in the volume of the desiccant.

"Fluid" refers to a substance in the form of a liquid or gas at room temperature and atmospheric pressure.

"High density polyethylene (HDPE)" refers to a polyethylene having a density of about 0.95 $g/cm^3$ or greater.

"Knife over roll coating" refers to a process in which a knife is positioned, with a specified gap, above a substrate that is moving beneath the knife on a moving roll. In this manner, the knife spreads a specified thickness of coating material onto the substrate.

"Layer" when used in the singular can have the dual meaning of a single element or a plurality of elements.

"Linear low density polyethylene (LLDPE)" refers to polymers of ethylene and higher alpha-olefin comonomers such as $C_3$–$C_{12}$ comonomers, and combinations thereof, having a density of about 0.900 to 0.935 $g/cm^3$.

"Low density polyethylene (LDPE)" refers to a polyethylene having a density between about 0.91 and about 0.925 $g/cm^3$.

"Modifying agent" refers to a substance that may be added to a composition to modify the physical properties of the composition, such as the color or texture of the composition.

"Monomer(s)" as used herein includes monomers, oligomers, polymers, mixtures of monomers, oligomers and/or polymers, and any reactive chemical species which are capable of copolymerization with monoethylenically unsaturated carboxylic, sulphonic or phosphonic acid or salts thereof.

"Nonwoven" or "nonwoven web" refers to materials and webs or material having a structure of individual fibers or filaments which are interlaid, but not in an identifiable manner as in a knitted fabric. The terms "fiber" and "filament" are used interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

"Roll printing" or "roll coating" refers to a process in which the application of a deposited material, generally as a paste, onto a substrate is carried out by transferring the deposited material from a roll onto the substrate in a more or less uniform layer using one or more rolls, which may be engraved, and a pool cylinder. A doctor blade is used to scrape any excess deposited material from the rolls or substrate. The doctor blade may be flat or have a patterned edge such as slots or ridges.

"Rotary screen printing" or "rotary screen coating" refers to a process that is a combination of roll printing or coating and screen printing or coating.

"Screen printing" or "screen coating" refers to a method of applying a deposited material by forcing the material to be deposited through a screen that may have uniform openings or patterned openings.

"Stranded composites" refer to sheets of material to which strands of an elastomeric material are adhered to create an elastomeric composite.

"Superabsorbent" refers to a water-swellable, water-insoluble organic or inorganic material capable, under the most favorable conditions, of absorbing at least about 10 times its own weight, or at least about 15 times its own weight, or at least about 20 times its own weight, or at least about 25 times its own weight in an aqueous solution containing 0.9 weight percent sodium chloride. The superabsorbent materials can be natural, synthetic, and modified natural polymers and materials. Superabsorbent materials differ from desiccant components (desiccants) in that absorbency is typically driven by osmotic pressure resulting in incorporation of water without chemical bonds, and accompanied by a substantial increase in volume of the superabsorbent material.

"Ultra low density polyethylene (ULDPE)" refers to polymers of ethylene and higher alpha-olefin comonomers such as $C_3$–$C_{12}$ comonomers, and combinations thereof, having a density of about 0.860 to less than 0.900 g/cm$^3$.

"Unit" or "polymer unit" refers to a monomer or polymer portion of a copolymer molecule or blend component that includes a different molecular structure, compared to another portion of the copolymer or blend component.

DESCRIPTION OF PREFERRED EMBODIMENTS

The present invention is directed to an absorbent binder desiccant composition that includes an absorbent binder (hydrophilic polymer) component having the capability of post-application, moisture-induced crosslinking and a desiccant component. The present invention further includes an absorbent binder desiccant structure formed by the crosslinking reaction. The present invention further includes a method of making and applying such an absorbent binder desiccant composition, and articles which utilize the absorbent binder desiccant composition and structure. The absorbent binder desiccant composition and structure can provide fluid retention properties in addition to adhesive properties. The absorbent binder desiccant composition and structure are particularly suitable for use in absorbent packaging applications where humidity reduction is important.

The absorbent binder desiccant composition includes the absorbent binder component and desiccant component in dry weight ratios of about 100:0 to about 1:10, suitably about 100:1 to about 1:10, suitably about 50:1 to about 1:5, particularly about 10:1 to about 1:3. The weight ratio of absorbent binder to desiccant may vary depending on the types of absorbent binder and desiccant used, the specific application, the amount and duration of the humidity reduction that is needed, and the temperature of the environment. Because the absorbent binder component may itself exhibit desiccant properties, the additional desiccant component may not be required in some applications The absorbent binder component provides a water-soluble ionic polymer capable of sufficient spontaneous crosslinking within about 10 minutes, at a temperature of about 120° C. or less, to reach an absorbent capacity of at least one gram of fluid per gram of absorbent binder component, suitably at least three grams of fluid per gram of absorbent binder component, using the centrifuge retention capacity test described herein. The term "spontaneous" crosslinking refers to crosslinking which occurs without radiation, catalysis, or any other inducement other than the specified temperature of about 120° C. or less, suitably about 100° C. or less. Eliminating the need for radiative crosslinking provides a significant processing advantage. The crosslinking at temperatures of about 120° C. or less, suitably about 100° C. or less, permits the absorbent binder desiccant composition to be applied to a substrate such as an absorbent article, and then crosslinked without degrading or damaging the substrate. The crosslinking occurs within about 10 minutes, suitably within about 8 minutes, particularly within about 6 minutes provides an efficient, commercially feasible, cost-effective crosslinking process. The ionic polymer may bear a positive charge, a negative charge, or a combination of both, and should have an ionic unit content of about 15 mole percent or greater. The ionic polymer may include a variety of monomer units described above, and suitably contains a carboxyl group-containing unit or a quaternary ammonium-containing unit.

The absorbent binder component includes at least 15 mass percent monoethylenically unsaturated carboxylic, sulphonic or phosphoric acid or salts thereof and an acrylate or methacrylate ester that contains an alkoxysilane functionality which, upon exposure to water, forms a silanol functional group which condenses to form a crosslinked polymer.

Suitable monoethylenically unsaturated monomers that may be included in the absorbent binder component include carboxyl group-containing monomers: monoethylenically unsaturated mono or poly-carboxylic acids, such as (meth) acrylic acid (meaning acrylic acid or methacrylic acid; similar notations are used hereinafter), maleic acid, fumaric acid, crotonic acid, sorbic acid, itaconic acid, and cinnamic acid;

Carboxylic acid anhydride group-containing monomers: monoethylenically unsaturated polycarboxylic acid anhydrides (such as maleic anhydride);

Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate), sodium maleate, methylamine maleate;

Sulfonic acid group-containing monomers: aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

Sulfonic acid salt group-containing monomers: alkali metal salts, ammonium salts, amine salts of sulfonic acid group containing monomers as mentioned above;

Quaternary ammonium salts; and/or

Amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide], N,N-dihydroxyalkyl (meth)acrylamides [such as N,N-dihydroxyethyl (meth)acrylamide], vinyl lactams (such as N-vinylpyrrolidone).

Suitably, the amount of monoethylenically unsaturated monomer(s) relative to the weight of the absorbent binder component may range from about 15 to about 99.9 weight percent. Typically, the monoethylenically unsaturated monomer levels may be between about 25% and about 90% of the weight of the absorbent binder component; particularly between about 30% and about 80% of the weight of the absorbent binder component; or between about 50% and about 70% of the weight of the absorbent binder component for some intended uses.

Organic monomers capable of co-polymerization with monoethylenically unsaturated monomers, which monomers contain a trialkoxy silane functional group or a moiety that reacts with water to form a silanol group, are useful in the practice of this invention. The trialkoxy silane functional group has the following structure:

wherein $R_1$, $R_2$ and $R_3$ are alkyl groups independently having from 1 to 6 carbon atoms. The term "monomer(s)" as used herein includes monomers, oligomers, polymers, mixtures of monomers, oligomers and/or polymers, and any other reactive chemical species which is capable of co-polymerization with monoethylenically unsaturated carboxylic, sulphonic or phosphoric acid or salts thereof, quaternary ammonium salts, or other monomers. Ethylenically unsaturated monomers containing a trialkoxy silane functional group are appropriate for this invention and are desired. Desired ethylenically unsaturated monomers include acrylates and methacrylates. A particularly desirable ethylenically unsaturated monomer containing a trialkoxy silane functional group is methacryloxypropyl trimethoxy silane, commercially available from Dow Corning, having offices in Midland, Mich., under the trade designation Z-6030 Silane. Other suitable ethylenically unsaturated monomers containing a trialkoxy silane functional group include, but are not limited to, methacryloxyethyl trimethoxy silane, methacryloxypropyl triethoxy silane, methacryloxypropyl tripropoxy silane, acryloxypropylmethyl dimethoxy silane, 3-acryloxypropyl trimethoxy silane, 3-methacryloxypropylmethyl diethoxy silane, 3-methacryloxypropylmethyl dimethoxy silane, and 3-methacryloxypropyl tris(methoxyethoxy) silane. However, it is contemplated that a wide range of vinyl and acrylic monomers having trialkoxy silane functional groups or a moiety that reacts easily with water to form a silanol group, such as a chlorosilane or an acetoxysilane, provide the desired effects are effective monomers for copolymerization in accordance with the present invention.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. Such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

The amount of organic monomer having trialkoxy silane functional groups or silanol-forming functional groups relative to the weight of the absorbent binder component may range from about 0.1 to about 15 weight percent. Suitably, the amount of monomer should exceed 0.1 weight percent in order provide sufficient crosslinking upon exposure to moisture. Typically, the monomer addition levels are between about 0.1% and about 20% of the weight of the absorbent binder component; particularly, between about 1.0% and about 10% of the weight of the absorbent binder component; or between about 1.5% and about 5.5% of the weight of the absorbent binder component for some intended uses.

Optionally, the absorbent binder component may include long chain, hydrophilic monoethylenically unsaturated esters, such as poly(ethylene glycol) methacrylate having from 1 to 13 ethylene glycol units. The hydrophilic monoethylenically unsaturated esters have the following structure:

The amount of monoethylenically unsaturated hydrophilic esters relative to the weight of the absorbent binder component thereof may range from about 0 to about 75 weight percent of monomer to the weight of the absorbent binder component. Typically, the monomer addition levels are between about 10% and about 60% of the weight of the absorbent binder component; particularly, between about 20% and about 50% of the weight of the absorbent binder component; or between about 30% and about 40% of the weight of the absorbent binder component for some intended uses.

The absorbent binder component may be prepared by adding a solution of the above monomers to an initiator solution, at a suitable temperature to generate free radicals, for example between about 50 and about 90 degrees Celsius. An initiator solution may be prepared by dissolving an initiator in a solvent. Possible solvents include, but are not limited to, alcohols such as ethanol. A variety of initiators may be useful in the practice of this invention. The polymerization initiator may be activated using a variety of methods including, but not limited to, thermal energy, ultraviolet light, redox chemical reactions. A suitable class of initiators are organic peroxides and azo compounds, with benzoyl peroxide and azobisisobutyronitrile (AIBN) as examples.

Compounds containing an O—O, S—S, or N=N bond may be used as thermal initiators. Compounds containing O—O bonds; i.e., peroxides, are commonly used as initiators for polymerization. Such commonly used peroxide initiators include: alkyl, dialkyl, diaryl and arylalkyl peroxides such as cumyl peroxide, t-butyl peroxide, di-t-butyl peroxide, dicumyl peroxide, cumyl butyl peroxide, 1,1-di-t-butyl peroxy-3,5,5-trimethylcyclohexane, 2,5-dimethyl-2,5-di(t-butylperoxy)hexane, 2,5-dimethyl-2,5-bis(t-butylperoxy)hexyne-3 and bis(a-t-butyl peroxyisopropylbenzene); acyl peroxides such as acetyl peroxides and benzoyl peroxides; hydroperoxides such as cumyl hydroperoxide, t-butyl hydroperoxide, p-methane hydroperoxide, pinane hydroperoxide and cumene hydroperoxide; peresters or peroxyesters such as t-butyl peroxypivalate, t-butyl peroctoate, t-butyl perbenzoate, 2,5-dimethylhexyl-2,5-di(perbenzoate) and t-butyl di(perphthalate); alkylsulfonyl peroxides; dialkyl peroxymonocarbonates; dialkyl peroxydicarbonates; diperoxyketals; ketone peroxides such as cyclohexanone peroxide and methyl ethyl ketone peroxide. Additionally, azo compounds such as 2,2'-azobisisobutyronitrile abbreviated as AIBN, 2,2'-azobis(2,4-dimethylpentanenitrile) and 1,1'-azobis(cyclohexanecarbonitrile) may be used as the initiator.

The method for making the absorbent binder component can be carried out in a single step wherein polymerization and neutralization of the absorbent binder component is achieved. The polymerization/neutralization reaction is conducted in an aqueous medium thereby eliminating the need for organic solvents.

More specifically, the absorbent binder component can be made by combining a first aqueous monomer solution including a reducing polymerization initiator with a second aqueous monomer solution including an oxidizing polymerization initiator, wherein the initiators react to form the absorbent binder component. The first aqueous monomer solution further includes a monoethylenically unsaturated monomer and an ethylenically unsaturated monomer that contains an alkoxysilane functionality. The second aqueous monomer solution includes a monoethylenically unsaturated monomer. Suitably, the absorbent binder component is formed in about 100 minutes or less, or 60 minutes or less, desirably in about 30 minutes or less, or about 15 minutes or less, or in one embodiment about 10 minutes or less. The first and second aqueous monomer solutions may include any of the monoethylenically unsaturated monomers listed above.

In one embodiment, the first and/or second aqueous monomer solution may include a monoethylenically unsaturated monomer such as a carboxylic acid salt, a sulphonic acid salt, a phosphoric acid salt, a quaternary ammonium salt, or a combination thereof.

In another embodiment, the first and/or the second aqueous solution may include a monoethylenically unsaturated monomer such as a carboxylic acid, a sulphonic acid, a phosphoric acid or a combination thereof that may be at least partially neutralized or converted to the salt form in situ. In this embodiment, an amount of a basic material, such as sodium hydroxide, effective to at least partially neutralize the monoethylenically unsaturated monomer may be included in the first and/or second aqueous solution. Alternatively, the monoethylenically unsaturated monomer may be added to a basic solution such as, for example, a sodium hydroxide solution to form an aqueous monomer solution. Desirably, the monoethylenically unsaturated monomer in the first and/or second aqueous monomer solution is neutralized to provide a solution pH of about 5 to about 8 prior to polymerization with the ethylenically unsaturated monomer. One monoethylenically unsaturated monomer suitable for use in this embodiment includes acrylic acid.

Suitably, the pH of the first and/or second aqueous monomer solution is adjusted to about 6.5 to about 7.0. The pH of the first aqueous solution may be adjusted prior to the addition of the ethylenically unsaturated monomer. Desirably, the pH of the first aqueous monomer solution is adjusted prior to the addition of the reducing polymerization initiator. The pH of the second aqueous solution may be adjusted prior to the addition of the oxidizing polymerization initiator. Alternatively, the pH of the combined first and second aqueous monomer solutions may be adjusted to about 6.5 to about 7.0.

The first and second aqueous monomer solutions may include the monoethylenically unsaturated monomer in any suitable proportion to form an absorbent binder component including about 15 to about 99.9 composition weight percent monoethylenically unsaturated carboxylic, sulphonic or phosphoric acid or salt thereof, quaternary ammonium salt, or the like. Typically, the levels of monoethylenically unsaturated carboxylic, sulphonic or phosphoric acid or salts thereof in the absorbent binder component may be between about 25 and about 90 weight percent; particularly between about 30 and about 80 weight percent; or between about 50 and about 70 weight percent for some intended uses.

The first aqueous monomer solution also includes an organic monomer capable of co-polymerization with monoethylenically unsaturated carboxylic, sulphonic or phosphoric acid or salts thereof, or quaternary ammonium salts. The above-described organic monomers that contain a trialkoxy silane functional group or a moiety that reacts with water to form a silanol group, are useful in the practice of this invention. The above-described monomers capable of copolymerization that can subsequently be reacted with a compound containing a trialkoxysilane group or a moiety that reacts with water to form a silanol group, are also useful.

The first aqueous monomer solution may include the ethylenically unsaturated monomer containing a trialkoxy silane functional group in any suitable proportion to provide an absorbent binder composition including about 0.1 to about 20 composition weight percent of this monomer. Suitably, the amount of ethylenically unsaturated monomer containing a trialkoxy silane functional group should exceed 0.1 composition weight percent in order to provide sufficient crosslinking upon removal of water. Typically, the monomer addition levels are between about 0.1 and about 15 composition weight percent; particularly, between about 1.0 and about 10 composition weight percent; or between about 1.5 and about 5.5 composition weight percent for some intended uses.

In one embodiment, a surfactant may be added to the first and/or second aqueous monomer solution to disperse the ethylenically unsaturated monomer. One surfactant suitable for use in the present invention is a dioctyl sodium sulfosuccinate available under the trademark AEROSOL OT from Cytec Industries, Inc. of Paterson, N.J.

The first aqueous monomer solution further includes a reducing polymerization initiator. Suitable reducing polymerization initiators include, but are not limited to, ascorbic acid, alkali metal sulfites, alkali metal bisulfites, ammonium sulfite, ammonium bisulfite, alkali metal hydrogen sulfite, ferrous metal salts such as ferrous sulfates, sugars, aldehydes, primary and secondary alcohols, and combinations thereof. In one embodiment, the reducing polymerization initiator includes ascorbic acid.

The second aqueous monomer solution further includes an oxidizing polymerization initiator. Suitable oxidizing initiators include, but are not limited to, hydrogen peroxide, alkali metal persulfates, ammonium persulfate, alkylhydroperoxides, peresters, diacryl peroxides, silver salts, and combinations thereof. In one embodiment, the oxidizing polymerization initiator includes hydrogen peroxide.

Generally, when the first aqueous monomer solution is combined with the second aqueous monomer solution the reducing polymerization initiator reacts with the oxidizing polymerization initiator, e.g. a redox reaction, thereby initiating a polymerization reaction to form an absorbent binder component including a monoethylenically unsaturated monomer and an ethylenically unsaturated monomer that has post-application, moisture-induced crosslinking capability.

The desiccant component may be combined with the absorbent binder component any time prior to crosslinking of the absorbent binder component, to form the absorbent binder desiccant composition. Suitable desiccant components include without limitation anhydrous salts which absorb water or moisture to form a stable hydrated salt, capillary desiccants which rely on fine capillaries between adjacent desiccant particles to absorb moisture, and chemical desiccants which chemically react with water to form stable compounds. Examples of anhydrous salts include without limitation sodium acetate, calcium sulfate, zinc chloride, zinc bromide, calcium oxide, and combinations thereof. Examples of capillary desiccants include without limitation montmorillonite clay, molecular sieves (e.g., synthetic zeolites), silica gels, starches and the like.

The desiccant component can be combined with the absorbent binder component using any suitable mixing apparatus. One particularly suitable mixer is a Hobart Mixer Model N-50, manufactured by Hobart Canada in North York, Ontario.

The absorbent binder desiccant composition may be applied to a substrate and subsequently dried to form a cast film. Drying conditions should be selected to provide for removal of water from the desiccant component, as well as the absorbent binder component. Once the absorbent binder desiccant composition is applied to the substrate, crosslinking can be moisture-induced by hydrolysis and condensation of alkoxysilanes. For example, crosslinking can be induced by concentrating the absorbent binder desiccant composition on the substrate through the removal of the water to promote condensation of silanols generated by hydrolysis of alkoxysilanes. Typically, crosslinking begins at a solution concentration above about 30 percent by weight absorbent binder desiccant composition.

Alternatively, the absorbent binder desiccant composition may be applied to a substrate during the manufacturing process of absorbent packaging. In another embodiment, the absorbent binder desiccant composition may be applied to a substrate as a coating by itself, thereby serving as an absorbency additive. In either of these embodiments, the absorbent binder desiccant composition is suitably present in any concentration that provides a viscosity suitable for the application process. The composition may be applied to the substrate using any suitable application process, including knife over roll coating, or roll coating, either in a continuous coverage or a patterned coverage. Printing applications are other suitable application techniques, including gravure printing, screen, and jet printing. The absorbent binder desiccant composition may also be applied to the substrate using a spray application.

In another embodiment, the absorbent binder desiccant composition may be prepared using a continuous process wherein the polymerization and/or neutralization reaction is carried out in a suitable reactor that conveys the resulting binder composition, upon completion of the polymerization reaction and addition of the desiccant component, directly to an apparatus for applying the absorbent binder desiccant composition onto the substrate. Such a continuous process may be desirable where conditions, such as high heat, may cause premature crosslinking of the absorbent binder component that would hinder application of the absorbent binder desiccant composition onto the substrate.

In addition, modifying agents such as compatible polymers, plasticizers, colorants, and preservatives may be incorporated in the absorbent binder desiccant composition.

For some intended uses the absorbent binder desiccant composition provides very flexible coatings and should therefore have a glass transition temperature below about 30 degrees Celsius, or below about 10 degrees Celsius, or below about 5 degrees Celsius, as measured by Differential Scanning Calorimetry (DSC), and a bending modulus lower than the substrate to which they are applied. Suitable substrates to which the absorbent binder desiccant composition may be applied include, but are not limited to, nonwoven, woven, and knitted fabrics; cellulosic tissue sheets; plastic films, including polypropylene, low density polyethylene, high density polyethylene, linear low density polyethylene, and ultra low density polyethylene; LYCRA stranded composites; elastomer net composites, metals, and glass.

In one embodiment, the absorbent binder component of the absorbent binder desiccant composition includes polyolefin glycol and/or polyolefin oxide units for enhanced flexibility. This flexible absorbent binder component includes about 15 to about 99.8% by mass of monoethylenically unsaturated polymer units, suitably about 25 to about 89.5% by mass, particularly about 30 to about 79% by mass, or about 50 to about 70% by mass. Suitable monoethylenically unsaturated polymer units include without limitation monoethylenically unsaturated carboxylic acid units and salts thereof, monoethylenically unsaturated sulphonic acid units and salts thereof, and monoethylenically unsaturated phosphonic acid units and salts thereof, and monoethylenically unsaturated quaternary ammonium salts. Suitable monoethylenically unsaturated monomers that can be used to form the monoethylenically unsaturated polymer units include without limitation any of the monoethylenically unsaturated monomers described above.

This flexible absorbent binder component also includes about 0.1 to about 20% by mass of polyacrylate ester units, such as acrylate and/or methacrylate ester units, that include an alkoxysilane functionality. The acrylate and/or methacrylate ester units are copolymerized with the monoethylenically unsaturated monomer units. In particular, the flexible absorbent binder component may include about 0.5 to about 15% by mass of the acrylate and/or methacrylate ester units, for instance about 1.0 to about 10% by mass, for instance about 1.5 to about 5.5% by mass.

As described above, the alkoxysilane functionality is a functional group or moiety that reacts with water to form a silanol group. One suitable alkoxysilane group is the above-described trialkoxy silane group having the following structure:

wherein $R_1$, $R_2$ and $R_3$ are alkyl groups independently having from 1 to 6 carbon atoms. Any of the monomers described above, which contain the trialkoxysilane functional group, are suitable.

In addition to monomers capable of co-polymerization that contain a trialkoxy silane functional group, it is also feasible to use a monomer capable of co-polymerization that can subsequently be reacted with a compound containing a trialkoxy silane functional group or a moiety that reacts with water to form a silanol group. As described above, such a monomer may contain, but is not limited to, an amine or an alcohol. An amine group incorporated into the co-polymer may subsequently be reacted with, for example, but not limited to, (3-chloropropyl)trimethoxysilane. An alcohol group incorporated into the co-polymer may subsequently be reacted with, for example, but not limited to, tetramethoxysilane.

This flexible absorbent binder component also includes about 0.1 to about 75% by mass polyolefin glycol and/or polyolefin oxide units, suitably about 5 to about 75% by mass, particularly about 10 to about 60% by mass, particularly about 20 to about 50% by mass, particularly about 30 to about 40% by mass. The polyolefin glycol or oxide may be a glycol or oxide of an olefin polymer having about 2 to about 4 carbon atoms. Polyethylene glycol, polyethylene oxide, polypropylene glycol and polypropylene oxide are examples of suitable polymer units. The polyolefin glycol and/or polyolefin oxide may include on average about 30 to about 15,000 glycol and/or oxide units per molecule. The weight average molecular weight of polyolefin glycol units may range from about 200 to about 8000. When polyolefin oxide units are employed, they may have a weight average molecular weight of about 100,000 to about 600,000.

Polyolefin glycols and polyolefin oxides are commercially available, and are common. To prepare this flexible absorbent binder component, a pre-formed polyolefin glycol and/or oxide may be dissolved or dispersed in a reaction vessel which includes an aqueous solvent or carrier, an organic solvent or carrier such as ethanol, or a miscible combination of aqueous and organic solvent or carrier. The monomers used to form the monoethylenically unsaturated polymer units and the polyacrylate ester units are added to the solution and polymerized using a template polymerization process in which the polyolefin glycol or oxide serves as a template polymer. Before initiation, the polar groups of the monomers, for instance the acid groups of acrylic acid, are attracted to the polyolefin glycol and/or polyolefin oxide through hydrogen bonding. The steric alignment of the monomers, with the polyolefin glycol and/or oxide serving as backbone, aids in the polymerization and typically increases the chain length of the polymerizing unit. During the polymerization, radical polymerizing chains may become attached to the template polymer, resulting in grafting of polyolefin glycol and/or oxide to the copolymer being formed. However, this graft polymerization need not occur. The resulting flexible absorbent binder component includes the polyolefin glycol and/or oxide attached to, and/or blended with, the copolymer of the monoethylenically unsaturated polymer units and the acrylate or methacrylate ester units that include the alkoxysilane functionality.

The polymerization may be initiated using a variety of methods, including without limitation thermal energy, ultraviolet light, and redox chemical reactions. A solution of the above ingredients may be added to an initiator solution at a temperature suitable for generating free radicals, for instance about 50 to about 90° C. An initiator may be prepared by dissolving an initiator in an organic or aqueous solvent. A suitable class of initiators are organic peroxides and azo compounds, with benzoyl peroxide and azobisisobutylnitrile (ABN) as examples.

Compounds containing an O—O, S—S, or N=N bond may be used as thermal initiators. Any of the above-described thermal initiators can be used when preparing the flexible absorbent binder component.

Alternatively, redox initiation can be used to prepare the flexible absorbent binder component, as described above. The polyolefin glycol and/or polyolefin oxide may be added to the first monomer solution, or the second monomer solution, or both. Surfactants and other ingredients can also be added, as described above.

In one embodiment used to prepare the flexible absorbent binder component, the monoethylenically unsaturated polymer unit is a cationic polymer. The cationic polymer is advantageous because it provides a) inherent antimicrobial properties, b) enhanced attraction and retention into cellulose fibers in a suspension, and c) enhanced attraction to superabsorbent particles which are negatively charged. Suitable cationic polymers include those prepared by copolymerizing a monomer 1) selected from a) acryloyloxyethyl-trialkyl-substituted ammonium salts, b) acryloyloxypropyl-trialkyl-substituted ammonium salts, c) acrylamidoethyl-trialkyl-substituted ammonium salts, and d) acrylamidopropyl-trialkyl-substituted ammonium salts, with a monomer 2) selected from a) methacryl esters which contain an alkoxysilane group capable of moisture-induced crosslinking and b) acryl esters which contain an alkoxysilane group capable of moisture-induced crosslinking. Other monomers may also be present, for instance, an acrylic acid or acrylamide. The polymerization is conducted in the presence of a polyolefin glycol and/or polyolefin oxide as described above, suitably a polyethylene glycol. The cationic monoethylenically unsaturated monomer unit and the polyolefin glycol are present in the amounts described above.

The cationic monoethylenically unsaturated polymer may be prepared by a redox initiation process, according to the following reaction. The cationic copolymer is then combined with the desiccant component, coated and dried onto a substrate to form the crosslinked flexible absorbent binder desiccant structure.

-continued crosslinked, absorbent coating

Applications where the cationic flexible absorbent binder desiccant composition is useful include without limitation the coating of paper and plastic cartons for carrying hot food, the internal coating of lids in medicine bottles, and the internal coating of a wide variety of metal, glass and paper containers and packages to keep their contents dry.

The flexible absorbent binder desiccant composition may be applied to a substrate and subsequently dried to form an absorbent binder desiccant structure (e.g., a film). Once the flexible absorbent binder desiccant composition is applied to the substrate, crosslinking can be moisture-induced by hydrolysis and condensation of alkoxysilanes. For example, crosslinking of the flexible absorbent binder desiccant composition can be induced by concentrating the flexible absorbent binder desiccant composition on the substrate through the removal of the water to promote condensation of silanols generated by hydrolysis of alkoxysilanes. Typically, crosslinking begins at a solution concentration of about 30 percent or greater by weight of absorbent binder desiccant composition. Furthermore, if the substrate has hydroxyl group functionality on its surface, then the silanols within the binder composition may react with the hydroxyl groups to form a covalent bond between the binder and the hydroxyl-containing surface. Non-limiting examples of substrates with hydroxyl surface functionality include glass, sand and cellulose. The flexible absorbent binder composition need not be crosslinked following application to a substrate. The flexible absorbent binder desiccant composition can be applied to a substrate using any of the techniques described above.

In another embodiment, the absorbent binder desiccant composition can be applied to a release liner and subsequently dried to form an absorbent binder desiccant structure (e.g., film). The film may be inserted into a package to provide humidity protection, or may be joined to a substrate on one or both surfaces.

Alternatively, the absorbent binder component can be applied to a substrate or release liner and crosslinked, without adding the separate desiccant component. The absorbent binder component may itself serve as a desiccant, and possesses desiccant properties. The absorbent binder component need not be crosslinked following application to a substrate.

Figure 1:
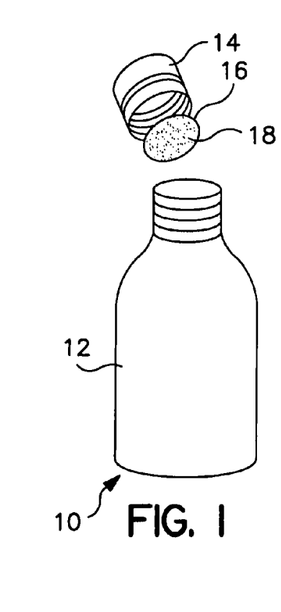
FIG. 1 illustrates a bottle, such as a medicine dropper, embodying the absorbent binder desiccant structure of the invention.

FIG. 1 illustrates a bottle 10, which can be a medicine bottle or other container in which there is a need to minimize the moisture exposure of the contents. The bottle 10 includes a base 12, a cap 14, and a lid 16 which fits inside the cap. The lid 16 can be formed entirely of an absorbent binder desiccant structure 18 of the invention. Alternatively, the lid 16 may be formed of paper, plastic or metal foil which is then coated with an absorbent binder desiccant composition, subsequently crosslinked to form an absorbent binder desiccant structure (e.g., a film). The absorbent binder desiccant structure may be of any suitable thickness and composition required to provide the desired level of moisture vapor absorption. The precise ingredients and weight ratios of the absorbent binder desiccant composition, including polymer type, desiccant type and amounts, may be optimized with this objective in mind.

Figure 2:
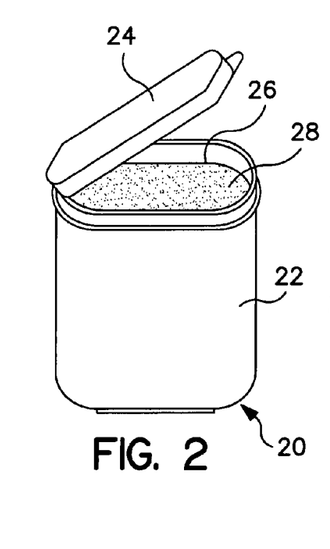
FIG. 2 illustrates a metal container embodying the absorbent binder desiccant structure of the invention.

FIG. 2 illustrates a food container 20 which can be formed of metal, plastic or thick paper (e.g., cardboard), and used to store sugar, salt, coffee, cocoa, or another food which is suitably maintained in a dry state. The food container 20 includes a body 22 and a lid 24. An absorbent binder desiccant structure 28 is formed on an entire inner surface 26 of the body 22 of the container 20. By surrounding the contents of container 20 with absorbent binder desiccant structure 18, maximum drying of the contents is maintained.

Figure 3:
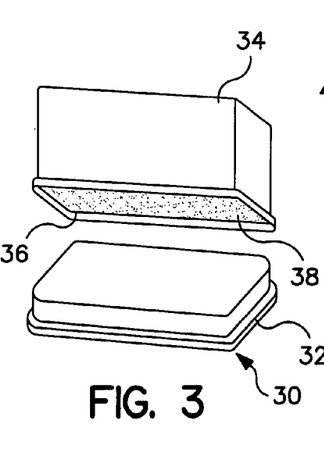
FIG. 3 illustrates a metal or plastic container embodying the absorbent binder desiccant structure of the invention.

FIG. 3 illustrates a bread box 30 including a base 32 and a cover 34. An entire inner surface 36 of cover 34 is coated with an absorbent binder desiccant structure 38. This bread box 30 is designed to control humidity, to alleviate molding of bread in a humid environment. The absorbent binder desiccant structure 38 should therefore be designed using absorbent binder and desiccant ingredients and amounts, which merely remove humidity from the air without causing excessive drying of the bread.

Figure 4:
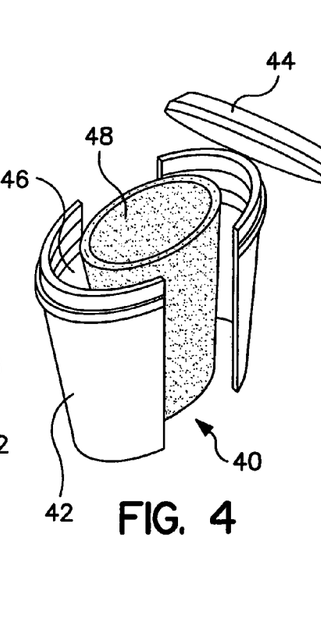
FIG. 4 illustrates a cup-like container of metal, plastic or foam, embodying the absorbent binder desiccant composition of the invention.

FIG. 4 illustrates a cup-shaped container 40 which can be used to store plant food, chemical powders or the like. Container 40 has a cup-shaped body 42 and a snap-on lid 44. An absorbent binder desiccant structure 48, having the shape of a cup, lines the inner surface 46 of body 42.

The above applications for the absorbent binder desiccant structure are merely exemplary. The absorbent binder desiccant composition and structure can be used in a wide variety of humidity control applications. The absorbent binder desiccant composition or structure can be applied to a substrate before or after crosslinking of the absorbent binder component, in alternative embodiments of the invention.

EXAMPLES

An absorbent binder composition was prepared from the following monomers using the following conditions.

Two monomer solutions were prepared separately. Solution No. 1 was prepared as follows. To 48.4 grams of a 80% solution of (2-acryloylethyl) trimethyl ammonium chloride (0.20 moles) was added 21.3 grams of deionized water, and 6.0 grams of PEG 200 (molecular weight 200). Then, 0.18 grams ($1.02 \times 10^{-3}$ moles) of ascorbic acid was added to the solution. This mixture was stirred with a magnetic stir bar at about 60 rpm in a bath of water at about 23° C. until the ascorbic acid was dissolved and the mixture cooled to 23° C.

Solution No. 2 was prepared in the following manner. 48.4 grams of a 80% solution of (2-acryloylethyl) trimethyl ammonium chloride (0.20 moles) was added 21.3 grams of deionized water, 6.0 grams of PEG 200 (molecular weight 200), 0.37 ml of 30% aqueous hydrogen peroxide and 1.0 ml ($5.42 \times 10^{-3}$ moles) of 3-(trimethoxysilyl)propyl methacrylate. This mixture was stirred with a magnetic stir bar at about 60 rpm in a bath of water at about 23° C. to provide a clear solution cooled to 23° C.

Solution No. 1 was placed into a water bath at 40° C. and Solution No. 2 was added to while stirring with a magnetic stir bar. A thermocouple was used to monitor the temperature and observe the reaction exotherm. The temperature of the water bath was raised to 60° C. over a time period of 15 minutes. 18 minutes after the solutions were combined, at a bath temperature of 60° C., an exotherm was evident by a rise in temperature to 72° C. over a period of 4 minutes and the solution became highly viscous. The reaction beaker was removed from the water bath after 60 minutes from the addition of Solution No. 2 to Solution No. 1. 150 grams of deionized water was added to reduce the polymer concentration to about 31%.

To 50 grams of the 31% polymer solution was added 2.5 ml of a 0.2% solution of hydrochloric acid. This solution was poured into two weighing dishes (100 cm² area) and the solution was dried for two days in the laboratory hood. The resultant film was very soft and flexible and slightly tacky. A portion of the film was cut off (0.5 gram) and soaked in 20 ml of 0.9% saline for 60 minutes. The film swelled and absorbed about 8000% of its dry weight of the saline solution.

Example 1

Silica gel, available from Aldrich Chemical Co., was crushed to a powder with a mortar and pestel. 3.5 grams of the crushed silica gel was mixed with 35 grams of the aqueous absorbent binder composition. Dissolution was aided by adding and mixing one gram of 0.25% by weight aqueous hydrochloric acid. Because the aqueous absorbent binder composition initially contained 20% by weight of absorbent binder component, the resulting absorbent binder desiccant composition contained the absorbent binder component and desiccant component in a weight ratio of 2:1. The absorbent binder desiccant composition was spread over a 5-inch by 6-inch area on a polypropylene spunbond fabric having a basis weight of 33 grams/m². A second piece of the same spunbond fabric was placed on top of the absorbent binder desiccant composition to create a sandwich structure. The sandwich structure was dried at 80° C. for one hour, crosslinking the absorbent binder desiccant composition to form an absorbent binder desiccant structure. The dried sandwich structure had a thickness of 1.7 mm.

Example 2

The same silica gel, available from Aldrich Chemical Co. and crushed to a powder, was added at 12 grams of silica gel into 30 grams of the same aqueous absorbent binder composition and 1 gram of 0.25% aqueous hydrochloric acid. Because the aqueous absorbent binder composition initially contained 20% by weight absorbent binder, the resulting absorbent binder desiccant composition contained the absorbent binder component and desiccant component in a weight ratio of 1:2. The absorbent binder desiccant composition was spread over a 7-inch by 7-inch area on a polypropylene spunbond fabric having a basis weight of 33 grams/m². A second piece of the same spunbond fabric was placed on top of the absorbent binder desiccant composition to create a sandwich structure. The sandwich structure was dried at 80° C. for one hour, crosslinking the absorbent binder desiccant composition to form an absorbent binder desiccant structure. The dried sandwich structure had a thickness of 3.0 mm.

Example 3 (Control)

Only the absorbent binder component was spread over a 4-inch by 4-inch area on a polypropylene spunbond fabric having a basis weight of 33 grams/m². A second piece of the same spunbond fabric was placed on top of the absorbent binder component to create a sandwich structure. The sandwich structure was dried at 80° C. for one hour, crosslinking the absorbent binder component. The dried sandwich structure had a thickness of 2 mm.

Example 4 (Control)

The same crushed silica gel, without the aqueous absorbent binder composition, was spread over a 3.14 square inch area aluminum weighing dish, 2 inches in diameter. The silica gel was dried at 80° for one hour, dehydrating the silica gel. The silica gel layer had a thickness of about 0.8 mm.

For each of Examples 1–4, the dry weight of the crosslinked absorbent binder desiccant structure, crosslinked absorbent binder component (without the desiccant component) or desiccant component (without the absorbent binder component) was determined by subtracting the weight of the spunbond fabric layers or weighing dish from the weight of the dried sandwich structure or loaded weighing dish. Samples of each sandwich structure or loaded weighing dish were placed in a controlled environment at 20° C. and 90% relative humidity for 24 hours. The samples were weighed at periodic intervals to determine their weight gain. The entire weight gain was attributed to moisture absorption by the absorbent binder component, and/or desiccant component or both, in each sample. The weight gains at each interval, as a percentage of the dry weight of the absorbent binder component and/or desiccant component, are plotted in FIG. 5.

Additional samples of each sandwich structure or loaded weighing dish were placed in a controlled environment at 20° C. and 50% relative humidity for 24 hours. The samples were weighed at periodic intervals to determine their weight gain. The weight gains at each interval, as a percentage of the dry weight of the absorbent binder component, desiccant component or both, are plotted in FIG. 6.

Figure 5:
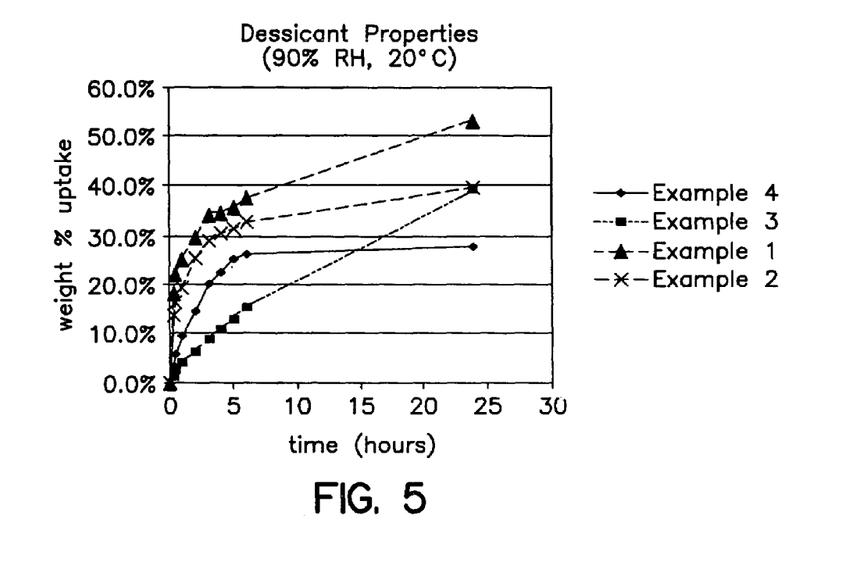
FIGS. 5 and 6 are plots illustrating the water intake properties of absorbent binder desiccant structures of the invention, at 20° C., at 92% and 50% relative humidity, respectively.
Figure 6:
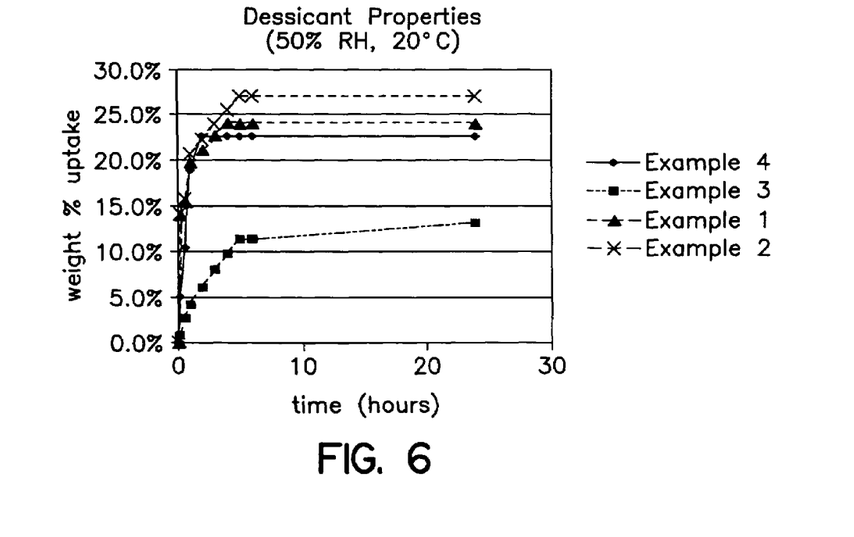

As shown in FIGS. 5 and 6, the absorbent binder desiccant structures (formed from the combinations of absorbent binder and desiccant) exhibited adequate desiccant properties. The absorbent binder desiccant structures have the added advantages of serving both as a binder and a containment medium for the particulate desiccant components.

TEST METHOD FOR DETERMINING ABSORBENT CAPACITY

As used herein, the Centrifugal Retention Capacity (CRC) is a measure of the absorbent capacity of the superabsorbent material retained after being subjected to centrifugation under controlled conditions. The CRC can be measured by placing a sample of the material to be tested into a water-permeable bag which will contain the sample while allowing the test solution (0.9 percent NaCl solution) to be freely absorbed by the sample. A heat-sealable tea bag material (available from Dexter Nonwovens of Windsor Locks, Conn., U.S.A., as item #1234T) works well for most applications. The bag is formed by folding a 5-inch by 3-inch sample of the bag material in half and heat sealing two of the open edges to form a 2.5-inch by 3-inch rectangular pouch. The heat seals should be about 0.25 inch inside the edge of the material. After the sample is placed in the pouch, the remaining open edge of the pouch is also heat-sealed. Empty bags are also made to be tested with the sample bags as controls. A sample size is chosen such that the teabag does not restrict the swelling of the material, generally with dimensions smaller than the sealed bag area (about 2-inch by 2.5-inch). Three sample bags are tested for each material.

The sealed bags are submerged in a pan of 0.9 percent NaCl solution. After wetting, the samples remain in the solution for 60 minutes, at which time they are removed from the solution and temporarily laid on a non-absorbent flat surface.

The wet bags are then placed into the basket of a suitable centrifuge capable of subjecting the samples to a g-force of 350. (A suitable centrifuge is a Heraeus LABOFUGE 400, Heraeus Instruments, part number 75008157, available from Heraeus Infosystems GmbH, Hanau, Germany). The bags are centrifuged at a target of 1600 rpm, but within the range of 1500–1900 rpm, for 3 minutes (target g-force of 350). The bags are removed and weighed. The amount of fluid absorbed and retained by the material, taking into account the fluid retained by the bag material alone, is the Centrifugal Retention Capacity of the material, expressed as grams of fluid per gram of material.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

What is claimed is:

1. An absorbent binder desiccant composition comprising water and a water-soluble ionic absorbent binder polymer having an alkoxysilane functionality and undergoing spontaneous crosslinking without a catalyst, radiation or other inducement within about 10 minutes after application to a substrate at a temperature of about 120° C. or less, to reach an absorbent capacity of at least one gram of fluid per gram of polymer using the centrifuge retention capacity test, and domains of at least one desiccant component mixed with and dispersed within the water-soluble absorbent binder polymer prior to crosslinking, wherein the absorbent binder polymer spontaneously crosslinks by hydrolysis of the alkoxysilane functionality and subsequent removal of the water after the absorbent binder desiccant composition is applied to the substrate.

2. The absorbent binder desiccant composition of claim 1, wherein the water-soluble ionic polymer and the desiccant component are present in a dry weight ratio of about 100:1 to about 1:10.

3. The absorbent binder desiccant composition of claim 1, wherein the water-soluble ionic polymer and desiccant are present in a dry weight ratio of about 10:1 to about 1:3.

4. The absorbent binder desiccant composition of claim 1, wherein the water-soluble ionic polymer undergoes spontaneous crosslinking within about 10 minutes at a temperature of about 120° C. or less, to reach an absorbent capacity of at least 3 grams of fluid per gram of polymer using the centrifuge retention capacity test.

5. The absorbent binder desiccant composition of claim 1, wherein the water-soluble ionic polymer comprises at least about 15 mole percent ionic polymer units.

6. The absorbent binder desiccant composition of claim 1, wherein the ionic polymer has a negative charge.

7. The absorbent binder desiccant composition of claim 6, wherein the ionic polymer comprises a carboxyl group-containing monomer.

8. The absorbent binder desiccant composition of claim 1, wherein the ionic polymer has a positive charge.

9. The absorbent binder desiccant composition of claim 8, wherein the ionic polymer comprises a quaternary ammonium group-containing monomer.

10. The absorbent binder desiccant composition of claim 8, wherein the ionic polymer comprises a reaction product of 1) a monomer selected from the group consisting of acryloyloxyethyl-trialkyl-substituted ammonium salts, acryloyloxypropyl-trialkyl-substituted ammonium salts, acrylamidoethyl-trialkyl-substituted ammonium salts, and acrylamidopropyl-trialkyl-substituted ammonium salts, with 2) a monomer selected from the group consisting of methacryl esters which contain an alkoxysilane group and acryl esters which contain an alkoxysilane group.

11. The absorbent binder desiccant composition of claim 1, wherein the desiccant component comprises a desiccant selected from the group consisting of sodium acetate, zinc chloride, zinc bromide, calcium oxide, calcium sulfate, montmorillonite clay, synthetic zeolites, synthetic gels, starches, and combinations thereof.

12. A combination comprising the absorbent binder desiccant composition of claim 1, and a substrate.

13. An absorbent binder desiccant composition comprising water, a water-soluble absorbent binder polymer component and domains of a desiccant component mixed with and dispersed within the water-soluble absorbent binder polymer component prior to crosslinking in a dry weight ratio of about 100:1 to about 1:10, wherein the absorbent binder polymer component comprises:
   a) about 15 to about 99.8% by mass of monoethylenically unsaturated polymer units;
   b) about 0.1 to about 20% by mass polyacrylate ester units that include an alkoxysilane functionality; and
   c) about 0.1 to about 75% by mass polymer units selected from the group consisting of polyolefin glycol units, polyolefin oxide units, and combinations thereof;
   and the absorbent binder polymer component spontaneously crosslinks without a catalyst, radiation or other inducement by hydrolysis of the alkoxysilane functionality and subsequent removal of the water after the absorbent binder desiccant composition is applied to a substrate.

14. The absorbent binder desiccant composition of claim 13, wherein the monoethylenically unsaturated polymer units and the polyacrylate ester units including an alkoxysilane functionality are copolymerized.

15. The absorbent binder desiccant composition of claim 13, wherein at least some of the polymer units selected from the group consisting of polyolefin glycol units, polyolefin oxide units, and combinations thereof are copolymerized with at least some of the polyacrylate ester units.

16. The absorbent binder desiccant composition of claim 13, wherein the absorbent binder component comprises about 25 to about 89.5% by mass monoethylenically unsaturated polymer units, about 0.5 to about 15% by mass ester units selected from the group consisting of acrylate and methacrylate ester units that include an alkoxysilane functionality, and about 10 to about 60% by mass of units selected from the group consisting of polyolefin glycol and polyolefin oxide units.

17. The absorbent binder desiccant composition of claim 13, wherein the absorbent binder component comprises about 30 to about 79% by mass monoethylenically unsaturated polymer units, about 1.0 to about 10% by mass ester units selected from the group consisting of acrylate and methacrylate ester units that include an alkoxysilane functionality, and about 20 to about 50% by mass of units selected from the group consisting of polyolefin glycol and polyolefin oxide units.

18. The absorbent binder desiccant composition of claim 13, wherein the monoethylenically unsaturated polymer units comprise a monomer unit selected from the group consisting of a carboxyl group-containing monomer, a carboxylic acid anhydride group-containing monomer, a carboxylic acid salt-containing monomer, a sulfonic acid group-containing monomer, an amide group-containing monomer, and a quaternary ammonium salt.

19. The absorbent binder desiccant composition of claim 13, wherein the alkoxysilane functionality comprises a trialkoxysilane group having the following structure:

wherein R1, R2 and R3 are alkyl groups independently having from 1 to 6 carbon atoms.

20. The absorbent binder desiccant composition of claim 13, wherein the absorbent binder component and desiccant component are present in a dry weight ratio of about 10:1 to about 1:3.

21. The absorbent binder desiccant composition of claim 13, wherein the desiccant component comprises a compound selected from the group consisting of sodium acetate, zinc chloride, zinc bromide, calcium oxide, calcium sulfate, montmorillonite clay, synthetic zeolites, synthetic gels, starches, and combinations thereof.

22. A combination comprising the absorbent binder desiccant composition of claim 13, and a substrate.

23. A combination of an absorbent binder desiccant structure and a substrate, wherein the absorbent binder desiccant structure is formed from water and an absorbent binder component comprising a water-soluble absorbent binder polymer having an alkoxysilane functionality and undergoing spontaneous crosslinking without a catalyst, radiation or other inducement within about 10 minutes after application to the substrate at a temperature of about 120° C. or less, to reach an absorbent capacity of at least one gram of fluid per gram of polymer using the centrifuge retention capacity test, and domains of a desiccant component mixed with and dispersed within the water-soluble absorbent binder polymer prior to crosslinking, wherein the absorbent binder polymer spontaneously crosslinks by hydrolysis of the alkoxysilane functionality and subsequent removal of the water after the absorbent binder component is applied to the substrate.

24. A humidity control package comprising the combination of claim 23.

25. A bottle comprising the combination of claim 23.

26. A can comprising the combination of claim 23.

27. A bread box comprising the combination of claim 23.

28. A cup comprising the combination of claim 23.

29. The combination of claim 23, wherein the absorbent binder component has a glass transition temperature of less than about 5° C.

30. The combination of claim 23, wherein the water-soluble polymer is crosslinked after being combined with the substrate.

31. The combination of claim 23, wherein the water-soluble polymer is crosslinked before being combined with the substrate.

32. The absorbent binder desiccant composition of claim 1, wherein the desiccant comprises an anhydrous salt.

33. The absorbent binder desiccant composition of claim 1, wherein the desiccant comprises a capillary desiccant.

34. The absorbent binder desiccant composition of claim 13, wherein the desiccant component comprises a compound selected from the group consisting of anhydrous salts, capillary desiccants, and combinations thereof.

35. The combination of claim 23, wherein the desiccant component comprises a compound selected from the group consisting of anhydrous salts, capillary desiccants and combinations thereof.

* * * * *